US011207680B2

(12) United States Patent
Lutnesky et al.

(10) Patent No.: US 11,207,680 B2
(45) Date of Patent: Dec. 28, 2021

(54) CASSETTES WITH A PROUD DIE

(71) Applicant: HEWLETT-PACKARD DEVELOPMENT COMPANY, L.P., Spring, TX (US)

(72) Inventors: Gary G. Lutnesky, Corvallis, OR (US); Dennis R. Esterberg, Corvallis, OR (US)

(73) Assignee: Hewlett-Packard Development Company, L.P., Spring, TX (US)

( * ) Notice: Subject to any disclaimer, the term of this patent is extended or adjusted under 35 U.S.C. 154(b) by 296 days.

(21) Appl. No.: 16/472,978

(22) PCT Filed: Feb. 3, 2017

(86) PCT No.: PCT/US2017/016508
§ 371 (c)(1),
(2) Date: Jun. 24, 2019

(87) PCT Pub. No.: WO2018/144016
PCT Pub. Date: Aug. 9, 2018

(65) Prior Publication Data
US 2020/0086316 A1 Mar. 19, 2020

(51) Int. Cl.
*A61J 1/06* (2006.01)
*B01L 3/00* (2006.01)
*G01N 21/00* (2006.01)
*B41J 2/175* (2006.01)

(52) U.S. Cl.
CPC ..... *B01L 3/502715* (2013.01); *B01L 3/50273* (2013.01); *B01L 3/502707* (2013.01); *B01L 2200/10* (2013.01); *B01L 2200/12* (2013.01); *B01L 2300/0645* (2013.01); *B01L 2300/0816* (2013.01); *B41J 2/1753* (2013.01)

(58) Field of Classification Search
CPC .......... B01L 3/502715; B01L 3/50273; B01L 3/502707; B01L 2200/10; B01L 2200/12; B01L 2300/0816; B01L 3/00; B41J 2/1753; A61J 1/06; G01N 21/00
See application file for complete search history.

(56) References Cited

U.S. PATENT DOCUMENTS

| 4,611,219 | A | 9/1986 | Sugitani et al. |
| 6,994,781 | B2 | 2/2006 | Cork et al. |
| D655,423 | S | 3/2012 | Nielsen et al. |
| 2004/0053290 | A1 | 3/2004 | Terbrueggen et al. |
| 2004/0166504 | A1 | 8/2004 | Rossier et al. |
| 2014/0193309 | A1 | 7/2014 | Still et al. |
| 2014/0297029 | A1 | 10/2014 | Peters |
| 2015/0367373 | A1 | 12/2015 | Dodd et al. |

FOREIGN PATENT DOCUMENTS

| WO | WO-2016032497 A1 | 3/2016 |
| WO | WO-2016122645 | 8/2016 |

OTHER PUBLICATIONS

Ashraf, M.W. et al.,; "Micro Electromechanical Systems (MEMS) Based Microfluidic Devices for Biomedical Applications"; Jun. 7, 2011; (cont. from above) https://www.ncbi.nlm.nih.gov/pmc/articles/PMC3131584/.

*Primary Examiner* — Brian J. Sines
(74) *Attorney, Agent, or Firm* — Fabian VanCott

(57) ABSTRACT

A cassette may include, in an example, a substrate, a die coupled to the substrate, and a reservoir defined in the substrate exposing a proximal side of the die to an external atmosphere wherein at least a portion of the die is proud relative to at least one surface of the substrate.

15 Claims, 14 Drawing Sheets

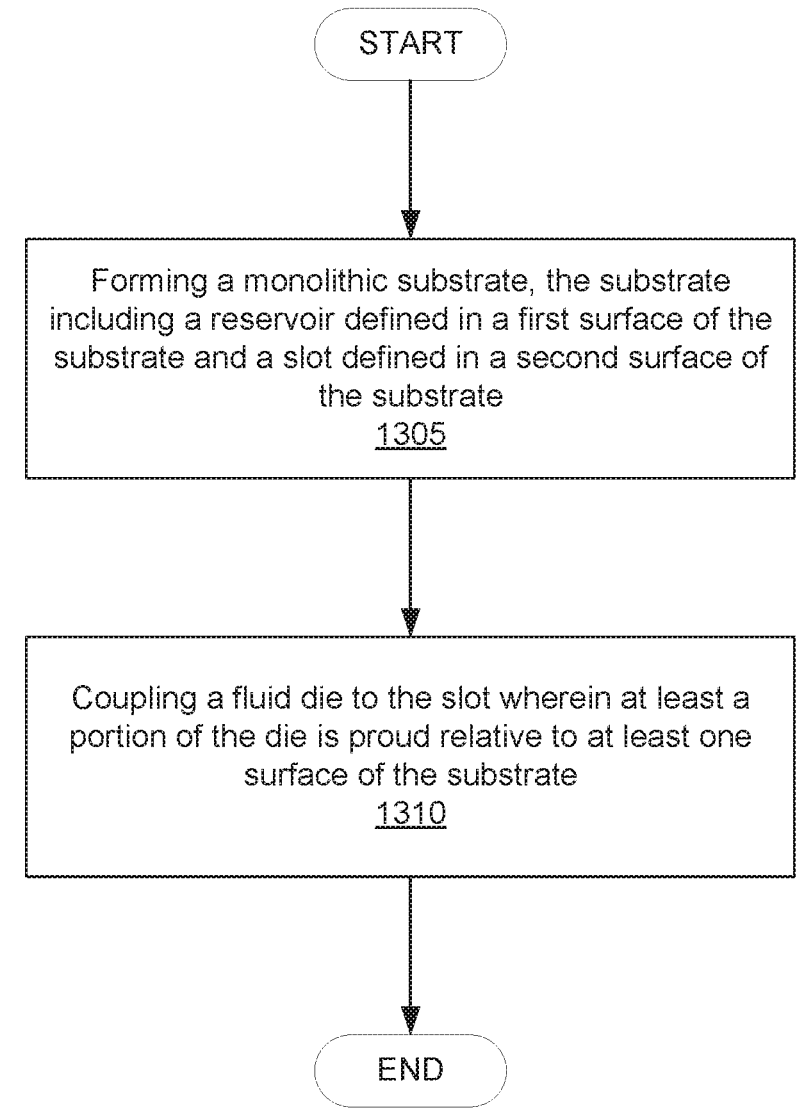

CASSETTES WITH A PROUD DIE

BACKGROUND

An "assay run" is an investigative or analytic event used in, for example, laboratory medicine, pharmacology, analytical chemistry, environmental biology, or molecular biology, for qualitatively assessing or quantitatively measuring the presence, amount, or the functional activity of a sample. The sample may be a drug, a genomic sample, a proteomic sample, a biochemical substance, a cell in an organism, an organic sample, or other inorganic and organic chemical samples. An assay run may measure an intensive property of the sample and express it in the relevant measurement unit such as, for example, molarity, density, functional activity in enzyme international units, degree of some effect in comparison to a standard, among other measurable characteristics. An assay may involve reacting a sample with a number of reagents, and may be classified as an instance of an assay procedure conforming to an assay protocol. An assay protocol may involve a set of reagent and/or sample fluids being dispensed in specific amounts to a number of assay reaction sites such as wells within an assay plate. Further, an assay protocol may include additional processing such as mixing, separation, heating or cooling, incubation, and eventually at least one read-out. The reproducibility and run-to-run comparability of an assay depends on the reproduction of its protocol.

BRIEF DESCRIPTION OF THE DRAWINGS

The accompanying drawings illustrate various examples of the principles described herein and are a part of the specification. The illustrated examples are given merely for illustration, and do not limit the scope of the claims.

FIG. 13 is a flowchart depicting a method of forming a cassette according to an example of the principles described herein.

Throughout the drawings, identical reference numbers designate similar, but not necessarily identical, elements.

DETAILED DESCRIPTION

Figure 1:
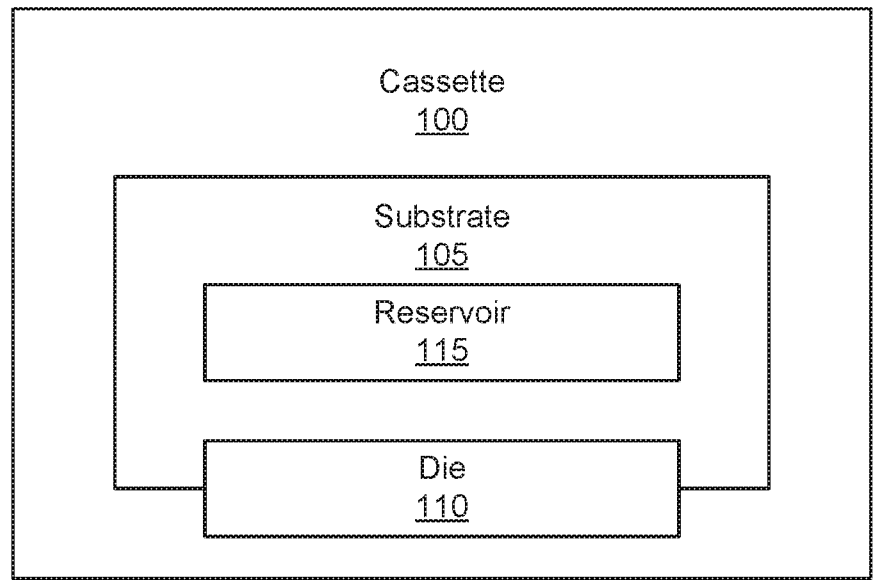
FIG. 1 is a block diagram of a cassette according to an example of the principles described herein.

Assay runs as described above have been done by hand using, for example a pipette. In order to complete the assay, a user may selectively take a sample using the pipette and eject a metered amount of the sample into individual wells of an assay plate. This is all done by hand and has proven to be relatively time consuming. Additionally, because a human is ejecting the samples into the individual wells of the assay plate, mistakes may be made and an extra amount of the sample may be added to any particular well or a portion of sample may not be added at all.

To place user interaction to a minimum, automated assay fluid dispensing systems have been developed that may dispense assay fluids, e.g., samples and reagents, in a precise, controlled fashion to multiple reaction sites within an assay plate in a short time. For example, a carefully formulated mixture of several reagents, including a target species of interest, may be carefully formulated at multiple reaction sites for the testing of a set of test sample reagents at multiple concentrations. This allows many reactions to proceed contemporaneously. The automation reduces user effort and user-caused variability, while the concurrency further reduces the time to complete a complex assay.

Some automated fluid ejection systems employ a fluid-ejection driver that uses interchangeable cassettes. The cassettes may contain assay fluids and may be controlled so that they deposit assay fluids onto reaction sites. For example, a reaction medium may be moved relative to the cassette so that, over a relatively short time, an assay fluid may be deposited in the same or varying amounts at different reaction sites of the reaction medium. The reaction medium may be, for example, a microtitre plate in which an array of reaction wells is defined, a tissue sample, a chip with integrated microfluidics, or a glass slide.

Cassettes can be used so that single or multiple fluids can be dispensed contemporaneously. For example, multiple samples can be deposited at respective reaction sites in parallel or quickly in serial in order to reduce the time to titrate a plurality of samples. Herein, "cassette" refers to a user-replaceable component of a dispenser system, through which at least one fluid flow through, respectively, at least one fluid channel before being dispensed from the dispensing system.

To provide better accuracy of the ejection of the fluids from the cassette, the present specification describes a die that is proud of an immediately adjacent surface of the cassette. Herein, a "proud" die is meant to be understood as a die that is raised above a surrounding area. In an example, the die is raised above an immediately surrounding area. Thus, in an example, a cassette may include a substrate, a die coupled to the substrate, and a reservoir defined in the substrate exposing a proximal side of the die to an external atmosphere wherein at least a portion of the die is proud relative to at least one surface of the substrate.

In an example, the distance from a distal surface of the die relative to the at least one surface of the substrate is approximately 40 micrometers. In an example, the distance from a distal surface of the die relative to the at least one surface of the substrate is approximately between 50 and 30 micrometers. In an example, the distance from a distal surface of the die relative to the at least one surface of the substrate is between a portion of a thickness of the die and the thickness of the die. In the examples above, the cassette may further include at least one rail formed on the at least one surface of the substrate, wherein the at least one rail protrudes past a plane of the distal surface of the die such that a thickness of the at least one rail relative to the at least one surface of the substrate defines a minimal distance between the distal surface of the die and an assay into which the die ejects a fluid.

The cassette may further include at least one slot fluidically coupling the reservoir to the die through the substrate. These examples above, may be exclusive examples or may be incorporated as combinations thereof in any manner to form the cassette described herein.

The present specification further describes a system for ejecting a fluid into an assay that may include at least one dispense head, the at least one dispense head may include a substrate, a die coupled to the substrate, and a reservoir defined in the substrate exposing a proximal side of the die to an external atmosphere with the system further including a controller to instruct the die to eject an amount of the fluid wherein a distance from a distal surface of the die relative to at least one surface of the substrate is approximately 40 micrometers.

In an example, a plurality of dispense head assemblies are included within the system with the dispense head assemblies being integrated into a frame.

In an example, the system may further include at least one rail formed on the at least one surface of the substrate wherein the at least one rail protrudes past a plane of the distal surface of the die. In an example or, alternatively, the examples above, a thickness of the at least one rail relative to the at least one surface of the substrate defines a minimal distance between the distal surface of the die and an assay into which the die ejects a fluid.

In an example or, alternatively, the examples above the system may include at least one slot fluidically coupling the reservoir to the die through the substrate. These examples above, may be exclusive examples or may be incorporated as combinations thereof in any manner to form the cassette described herein.

The present specification further describes a method of forming a cassette that may include forming a monolithic substrate, the substrate including a reservoir defined in a first surface of the substrate and a slot defined in a second surface of the substrate, the reservoir and the slot being fluidically coupled with the method further including coupling a fluid ejection die to the slot wherein at least a portion of the die is proud relative to at least one surface of the substrate.

In an example, the method of forming a cassette may include forming at least one rail on the at least one surface of the substrate, wherein the at least one rail protrudes past a plane of a distal surface of the die and wherein a thickness of the at least one rail relative to the at least one surface of the substrate defines a minimal distance between the distal surface of the die and an assay into which the die ejects a fluid.

In an example, the distance from a distal surface of the die relative to the at least one surface of the substrate is approximately 40 micrometers.

In an example, the distance from a distal surface of the die relative to at least one surface of the substrate is between a portion of a thickness of the die and the thickness of the die. These examples above, may be exclusive examples or may be incorporated as combinations thereof in any manner to form the cassette described herein.

As used in the present specification and in the appended claims, the term "a number of" or similar language is meant to be understood broadly as any positive number comprising 1 to infinity; zero not being a number, but the absence of a number.

In the following description, for purposes of explanation, numerous specific details are set forth in order to provide a thorough understanding of the present systems and methods. It will be apparent, however, to one skilled in the art that the present apparatus, systems, and methods may be practiced without these specific details. Reference in the specification to "an example" or similar language means that a particular feature, structure, or characteristic described in connection with that example is included as described, but may or may not be included in other examples.

FIG. 1 is a block diagram of a cassette (100) according to an example of the principles described herein. The cassette (100) may include a substrate (105) into which a reservoir (115) is formed and a die (110) coupled to the substrate.

The substrate (105) may be a monolithic piece of material. In an example, the substrate (105) is a thermoplastic material, doped with a non-conductive, metallic, inorganic compound. In this example, a number of metal traces may be added to any surface of the cassette (100) using a laser direct structuring (LDS) process. During the LDS process, the non-conductive, metallic, inorganic compounds are activated by a laser providing a surface into which a layer of conductive metal may be deposited using, for example, an electroless copper bath.

A reservoir (115) may be formed in to a surface of the substrate (105) so as to allow for a fluid such as an assay fluid or an analyte to be placed therein. The reservoir (155) provides the fluid to a die (110) coupled to the substrate (105). A slot may also be formed between the reservoir (1105) and the die (110) to direct the fluid towards the die using gravitational forces.

As mentioned, the die (110) is coupled to the substrate (105). The die (110) may include any number of layers of any type of material. In an example, the die (110) may include a silicon substrate having a rear exposed to atmosphere via the slot and reservoir (115) as described herein. The die (110) may further include a nozzle plate layer.

Any number of fluid outlets defined in the body of the die (110) opens into fluid chambers also defined in the silicon substrate. A number of firing resistors or piezoelectric devices are located within the fluid chambers and may be arranged in rows on opposite sides of the ink channels. A number of thin film metallic layers are deposited within the silicon substrate and these metallic layers are in electrical communication with the firing resistors or piezoelectric devices. The metallic layers may also be in electrical communication with a number of die pads formed on an exterior surface of the die (110). The die pads provide an electrical interface between a number of electrical traces formed on the surface of the substrate (105) so that electrical pulses may be provided to the firing resistors or piezoelectric devices during operation. The nozzle plate layer may have a number of nozzles defined therein providing fluidic communication between the chambers and atmosphere. The nozzle plate layer may be placed on top of the silicon substrate and may include various layers of insulating, conductive, and resistive material. In an example, the various layers that form the nozzle plate layer may be 40 micrometers thick.

In an example the die (110) is coupled to a surface of the substrate (105) opposite the surface of the substrate (105) the reservoir (115) is formed on. In this example, the reservoir (115) may provide access to a user in order for the user to deposit the fluid in the reservoir (115) for eventual delivery to the die (110) through a slot defined in the substrate (105) between the reservoir (115) and die (110).

At least a portion of the die (110) is proud relative to at least one surface of the substrate (105). In this example, at least a nozzle plate of the die (110) is proud relative to the surface of the substrate (105). In the examples provided herein, the surface of the substrate (105) is defined as that area immediately around the die (110). In these examples, the surface of the substrate (105) from which the die (110) is proud does not include any rails or other die (110) protective devices.

As described herein, at least one rail may be coupled to the substrate (105). During use of the cassette (100) in, for example, a system for ejecting a fluid into an assay, the rails provide a physical barrier between the die (110) and the assay into which the fluid is being ejected. This is accomplished by the at least one rail protruding past a plane of the distal surface of the die (110). This prevents damage to the die (110). Additionally, because the die (110) is proud relative to the surface of the substrate (105), ejection of the fluid into the assay may be accomplished with relatively more accuracy that if the die (110) was embedded entirely into the surface of the substrate (105). Thus, the thickness of the at least one rail relative to the surface of the substrate (105) defines a minimal distance between the distal surface of the die (110) and an assay into which the die (110) ejects a fluid.

The reservoir (115) may be any void defined in the surface of the substrate (105) opposite the die (110) that can hold an amount of fluid. In any of the examples described herein, the reservoir (115) may include a funnel that is fluidically coupled to a slot defined above the die (110). The reservoir (115) may expose a proximal side of the die (110) to an external atmosphere before a user adds a fluid into the reservoir. The fluid may be fed to the die (110) using gravity.

In an example, the distance from a distal surface or the surface of the nozzle plate of the die (110) relative to the at least one surface of the substrate is between a portion of a thickness of the die and the thickness of the die. In some examples, the die (110) is proud relative to the surface by protruding out from the surface any distance. In an example, the nozzle plate described above is the portion of the die (110) that protrudes out from the surface of the surface of the substrate (105). In this example, the nozzle plate thickness is 40 micrometers. This allows for the die pads described above to be placed even with a plane defined by the surface of the substrate (105) thereby allowing a number of wirebonds to be added to the die pads completing an electrical circuit between the traces and the firing resistors or piezoelectric devices.

Figure 2:
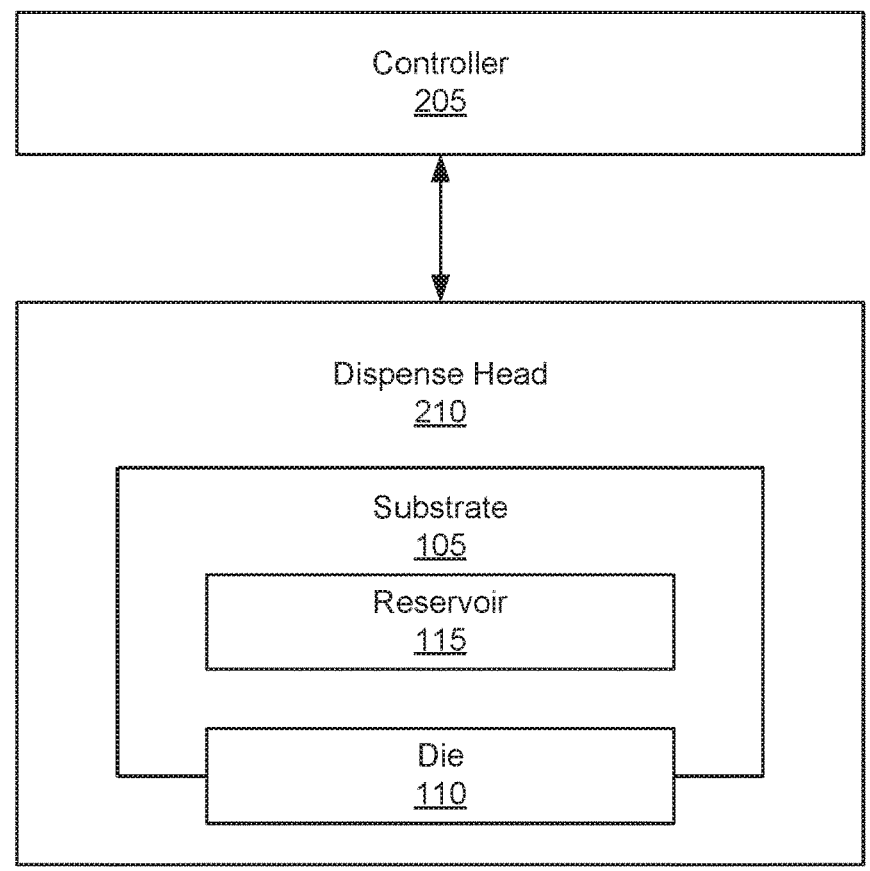
FIG. 2 is a block diagram of a system for ejecting fluid into an assay according to an example of the principles described herein.

FIG. 2 is a block diagram of a system (200) for ejecting fluid into an assay according to an example of the principles described herein. The system (200) may include a dispense head (210) and with a substrate (105). The substrate (105) may be similar to the substrate (105) as described in connection with FIG. 1. In this example, the substrate (105) includes a die (110) and reservoir (115).

The system (200) further includes a controller (205). The controller (205) directs the die (110) coupled to the substrate (105) to eject an amount of fluid therefrom and into a number of wells of an assay plate. The controller (205) may send a number of electrical signals to the die (110) via a number of contact pads and the electrical traces described above. In an example, the controller (205) may be a processor within the system (200) that directs the ejection of the fluid from the die (110). The controller (205) may execute computer usable program code stored in a memory device. The computer usable program code may provide to the controller (205) instructions that direct the timing of the ejection of the fluid as well as the amount of fluid to be ejected from the die (110) into the wells of the assay plate. The system (200) may further comprise servos and other mechanical devices to move the assay plate and/or the dispense head (210) such that the ejected fluid is ejected into a well within the assay plate as directed by the controller (205) executing the computer readable program code.

In an example, the dispense head may include any number of substrates (105), reservoirs (115), and/or dies (110). In an example, the number of substrates (105), reservoirs (115), and dies (110) is 1. In another example, the number of substrates (105), reservoirs (115), and dies (110) is four. In yet another example, the number of substrates (105), reservoirs (115), and dies (110) is eight.

Figure 3:
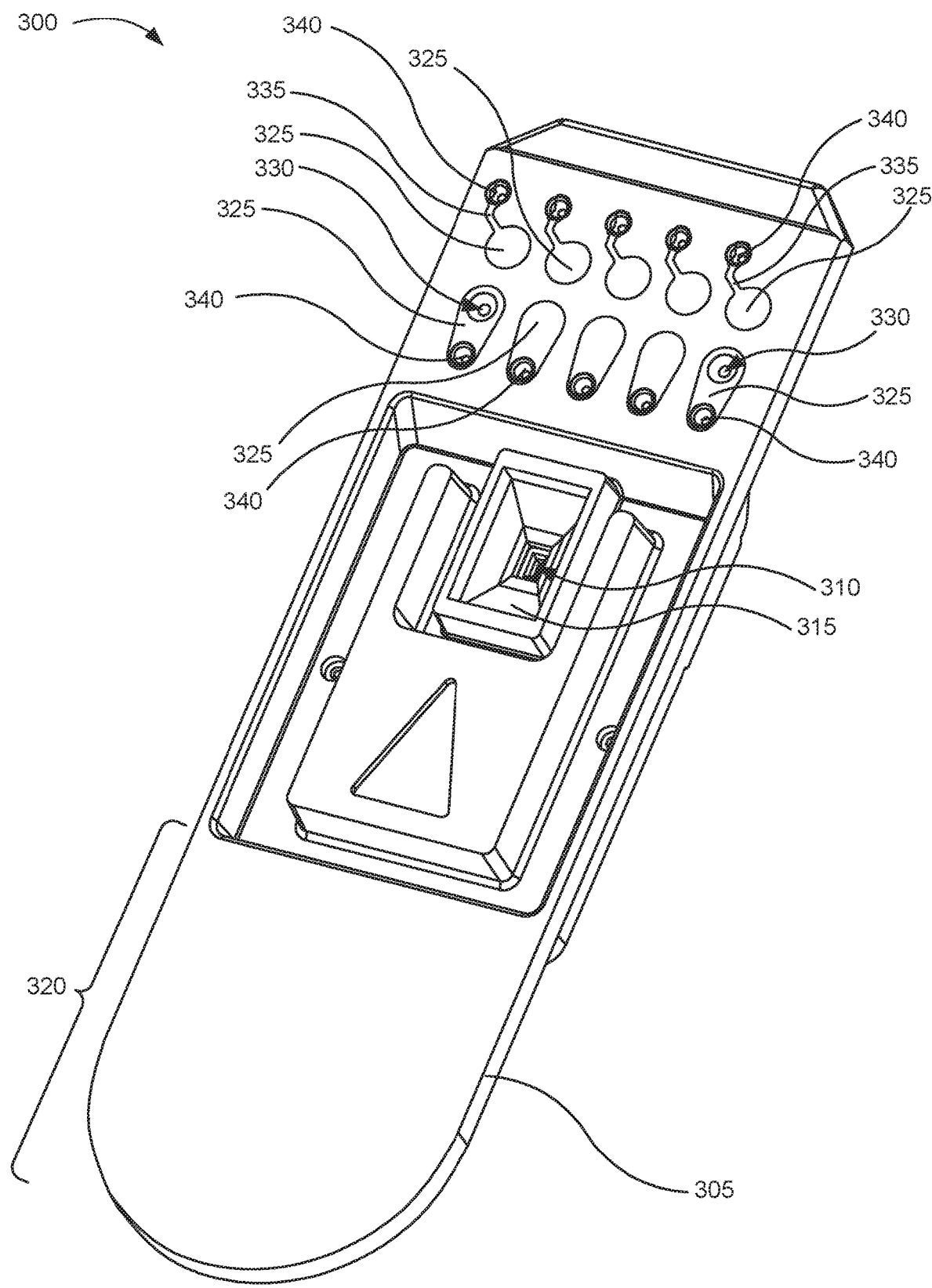
FIG. 3 is a front, perspective view of a cassette according to an example of the principles described here.

FIG. 3 is a front perspective view of a cassette (300) according to an example of the principles described here. As described above, the cassette (300) includes a substrate (305), a die (310) coupled to the substrate (305), and a reservoir (315) defined in the substrate (305). The cassette (300) with its substrate (305), die (310), and reservoir (315) may be similar to that cassette (FIG. 1, 100) as described in connection with FIG. 1.

The substrate (305) may be formed to allow a user to insert or otherwise interface the cassette (300) with a system for ejecting a fluid into an assay. In the example show in FIG. 3, the substrate (305) may include a handle (320). The handle (320) allows a user to grip the cassette (300) in order to manipulate the cassette (300) and place the cassette (300) into the system used to eject a fluid into an assay.

The cassette (300) may further includes a number of connection pads (325) and electrical traces (330) so that the die (310) of the cassette (300) can receive electrical signals directing when, where, and how to eject an amount of fluid therefrom. In an example, the cassette (300) is moved relative to an assay plate positioned below the cassette (300) such that placement of the die (310) over any portion of the assay plate and ejection of fluid from the die (310) allows an amount of fluid to be ejected into any number of wells formed in the assay plate. The ejection of the fluid from the die (310) is directed by a controller of the system for ejecting a fluid into an assay as described above.

Thus, in order to allows the cassette (300) to interface with the system for ejecting a fluid into an assay, the cassette (300) may include a number of contact pads (325) that interface with, for example, a number of pogo connectors on a printed circuit assembly (PCA). In the examples shown the figures of the present description the number of contact pads (325) is ten. However, the present specification contemplates the use of less or more contact pads (325). The number of contact pads (325) may be varied among different examples because the die (310) may receive signals from the PCA directing a number of microelectromechanical systems (MEMS) devices to be activated. Consequently, more or less contact pads (325) may be added or subtracted from those shown in FIG. 3 based on the number of signals used to activate any number of MEMS devices within the die (310). Not all of the contact pads (325) have been indicated in FIG. 3 in order to allow for better understanding of the cassette (300).

A number of the contact pads (325) may further include contact seats (330). The contact seats (330) may be used to allow for haptic feedback to a user inserting the cassette (300) into a system for ejecting a fluid into an assay. In an example, as the cassette (300) interfaces with the system (FIG. 2, 200), a number of pogo connectors may fall into the contact seats (330) allowing a user to know, via the haptic feedback, when the cassette (300) has properly interfaced with the system (FIG. 2, 200).

In an example, a number of traces (335) may electrically couple each of the contact pads (325) to a via (340). In other examples the contact pads (325) themselves may be electrically coupled to the their respective vias (340) without the use of traces (335).

In an example, the contact pads (325) and traces (335) may be formed onto the surface of the substrate (305) using a LDS process. Again, during the LDS process, the non-conductive, metallic, inorganic compounds are activated by a laser providing a surface into which a layer of conduct metal may be deposited using, for example, an electroless copper bath. The vias (340) may provide an electrical connection to a number of other traces (335) formed on an opposite side of the cassette (300).

Figure 4:
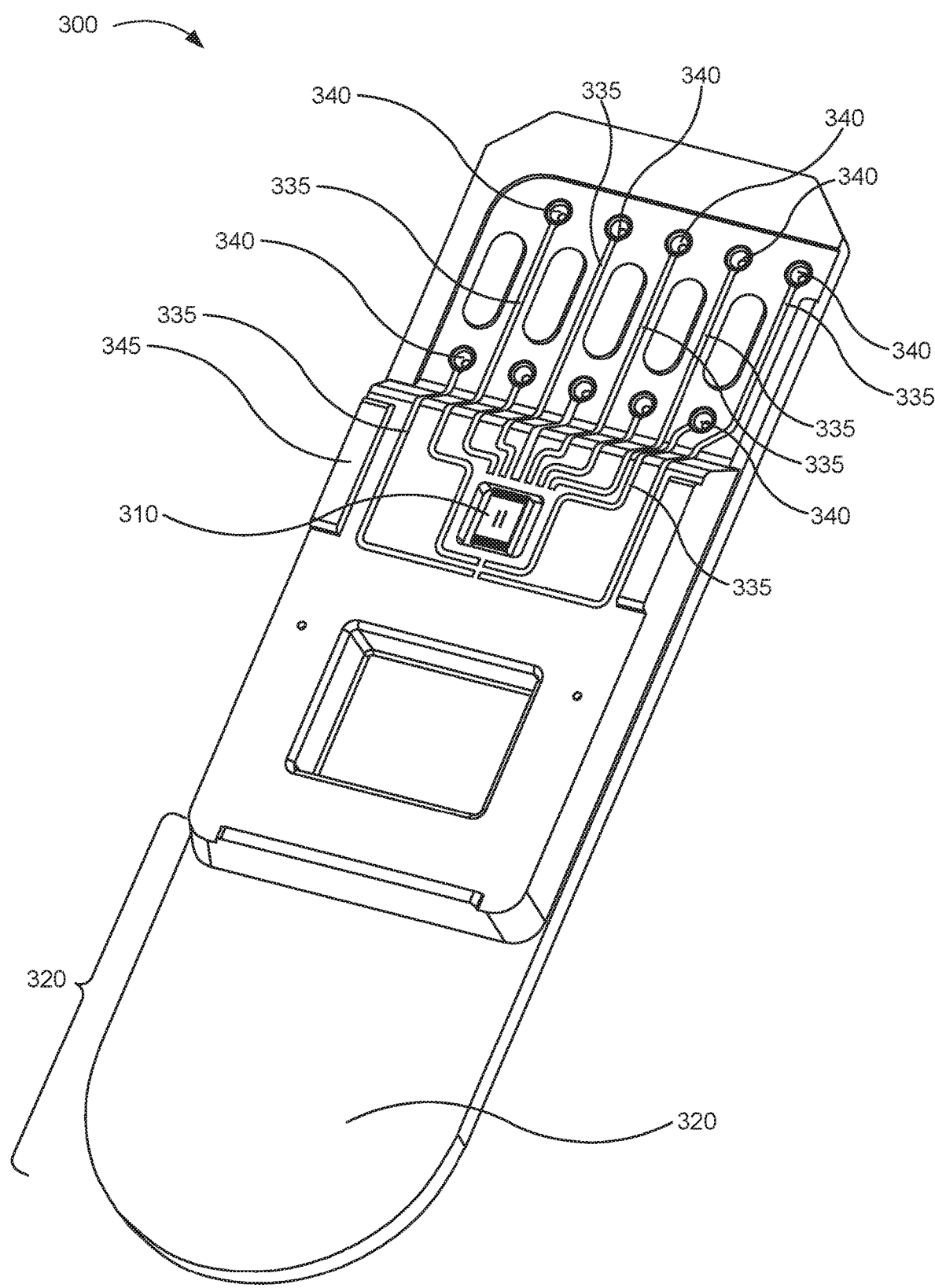
FIG. 4 is a back, perspective view of the cassette of FIG. 3 according to an example of the principles described herein.

FIG. 4 is a back, perspective view of the cassette (300) of FIG. 3 according to an example of the principles described herein. The vias (340) provide an electrical connection between the contact pads (325) on the front side of the cassette (300) to a number of traces (335) defined on the back side of the cassette (300). These traces (335) electrically couple each of the vias (340) to at least one die pad defined on the die (310). In this manner, a PGA may interface with the contact pads (325) defined on the front of the cassette (300) in order to send electrical signals to the die (310) to cause the die (310) to, at least, eject an amount of fluid therefrom.

The cassette (300) may further include a number of rails (345) defined on the substrate (305). In this example, the rails (345) provide a physical barrier from any object such as the assay plate from coming in contact with the die (310) and potentially damaging the die (310). Thus, a plane defined by a bottom portion of the rails (345) may be lower than a distal side of the die (310). During operation, the rails (345) may pass across the assay plate thereby keeping the die (310) from contacting the assay plate. Any number of rails (345) may be defined in the substrate (305) and the present specification contemplates the use of any number of rails (345).

As described above, the cassette (300) of FIGS. 3 and 4 includes a reservoir (315). The reservoir (315), in this example, may generally be in the form of a funnel shape such that a user, during operation, may provide an amount of fluid therein. The funnel shape of the reservoir (315) may funnel the fluid to a slot defined above a proximal side of the die (310). Thus, the funnel shaped reservoir (315) as shown in FIGS. 3 and 4, may provide a constant supply of fluid to the die (310) using gravitational forces.

Figure 5:
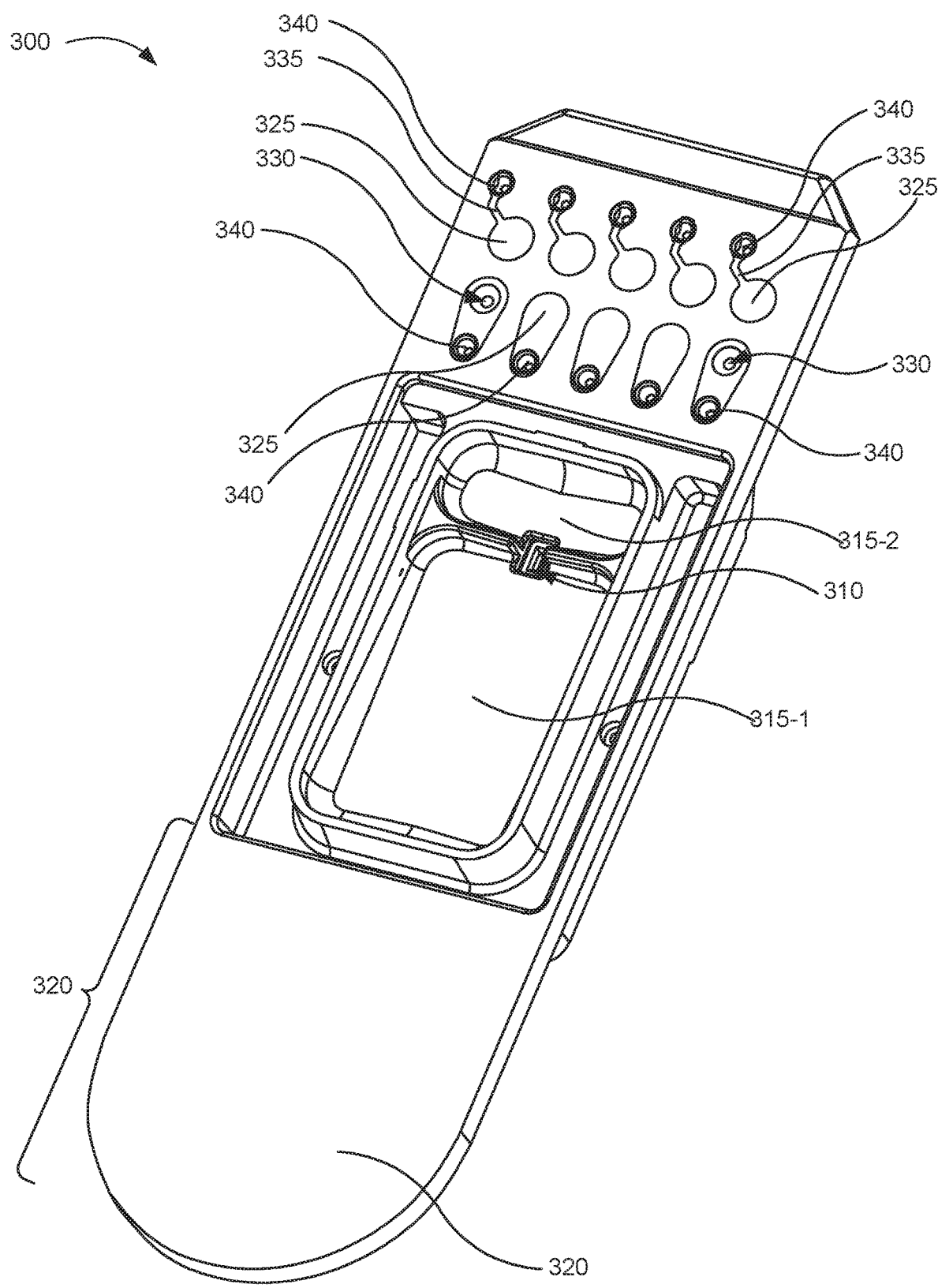
FIGS. 5 and 6 show a front perspective and back perspective view an alternative example of the cassette of FIGS. 3 and 4 according to an example of the principles described herein.
Figure 6:
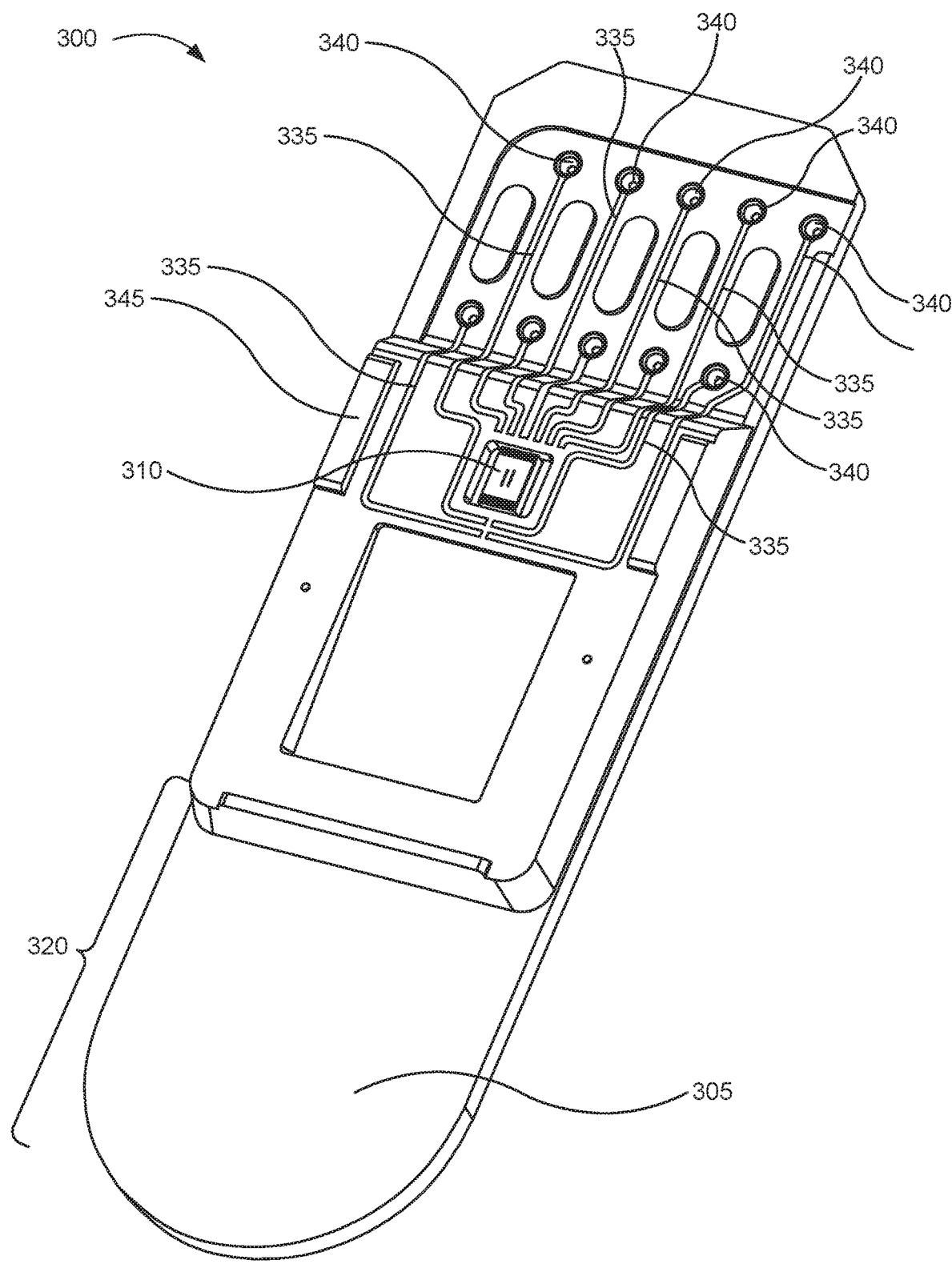

FIGS. 5 and 6 show a front perspective and back perspective view of an alternative example of the cassette (300) of FIGS. 3 and 4 according to an example of the principles described herein. FIGS. 5 and 6 show a cassette (300) including a substrate (305), die (310), reservoir (315), and handle (320) as described above. Similarly, the cassette (300) of FIGS. 5 and 6 includes those contact pads (325), contact seats (330), traces (335), and vias (340) already described in connection with FIGS. 3 and 4. These elements provide similar functions as described above and will not be repeated again.

The reservoir (315) of the cassette (300) shown in FIGS. 5 and 6, however, is a relatively larger reservoir (315) that may hold an additional amount of fluid. Additionally, the reservoir (315) of FIGS. 5 and 6 may be bifurcated into a first reservoir portion (315-1) and a second reservoir portion (315-2). The first and second reservoir portions (315-1, 315-2) may be used to introduce the fluid into the reservoir (315) for processing and ejection by the die (310). Thus, the reservoir (315) shown in FIGS. 3 and 4 and FIGS. 5 and 6 also shows that a reservoir (315) may be defined in the substrate (305) such that it may hold any amount and type of fluid so that these various amounts and types of fluids may be ejected from the die (310). In one example, the reservoir (315) of FIGS. 3 and 4 may be sized to contain approximately 20 microliters of fluid, while the reservoir (315) of FIGS. 5 and 6 may be sized to contain a fluid volume greater than 20 microliters.

Figure 7:
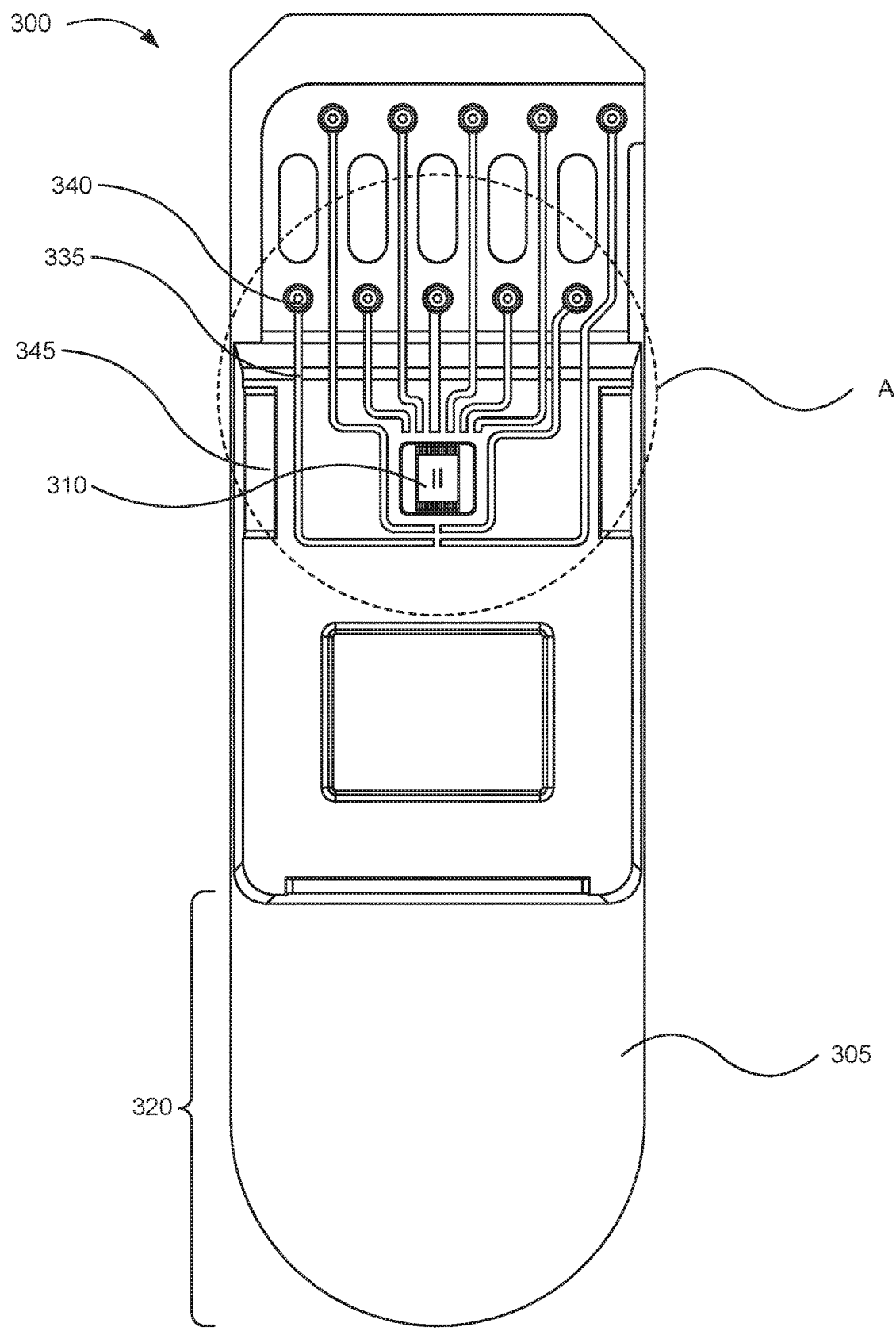
FIGS. 7 and 8 show a front elevational view of a back side of a cassette (300) and a blown-up portion of that cassette (300), respectively, according to an example of the principles described herein.
Figure 8:
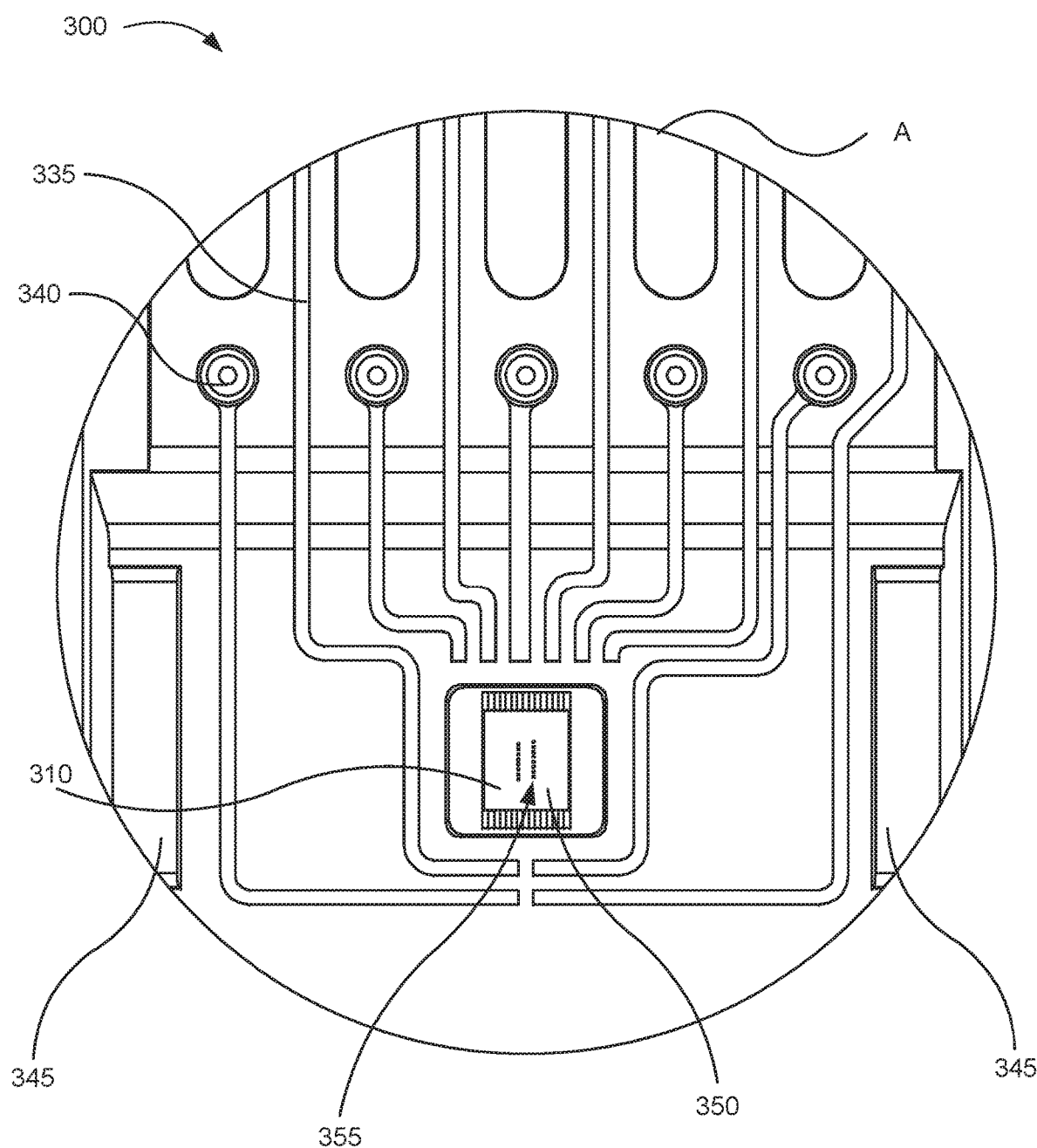

FIGS. 7 and 8 show a front elevational view of a back side of a cassette (300) and a blown-up portion of that cassette (300), respectively, according to an example of the principles described herein. Circle A represents that portion of the cassette (300) blown-up and shown in FIG. 8.

FIGS. 7 and 8 show similar elements as indicated in FIGS. 3-6 and are labeled accordingly and will not be described again. FIG. 8 in particular shows, in addition to those elements of FIGS. 3-6, a die (310) with a nozzle plate (350) and a number of nozzles (355) defined in the nozzle plate (350). As described above, the die (310) may include a number of fluidic channels and chambers through which the fluid placed in the reservoir (315) may flow through and out of the nozzles (355) of the nozzle plate (350). The fluid is ejected out of the nozzles (355) when a resistor or piezoelectric device causes the fluid to be ejected out. The ejection of the fluid is selectively accomplished by receiving any number of electrical signals via the contact pads (325), through the vias (340) and traces (335) and at a number of die (310) pads defined on the die (310). Although, FIG. 8 shows two rows of eight nozzles (355), the number of rows of nozzles (355) and nozzles (355) may be more or less than that shown in order to fit a particular goal of the cassette (300). For example, more nozzles (355) may be defined in the nozzle plate (350) in order to eject relatively more fluid out of the die (310).

Figures 9A, 9B:
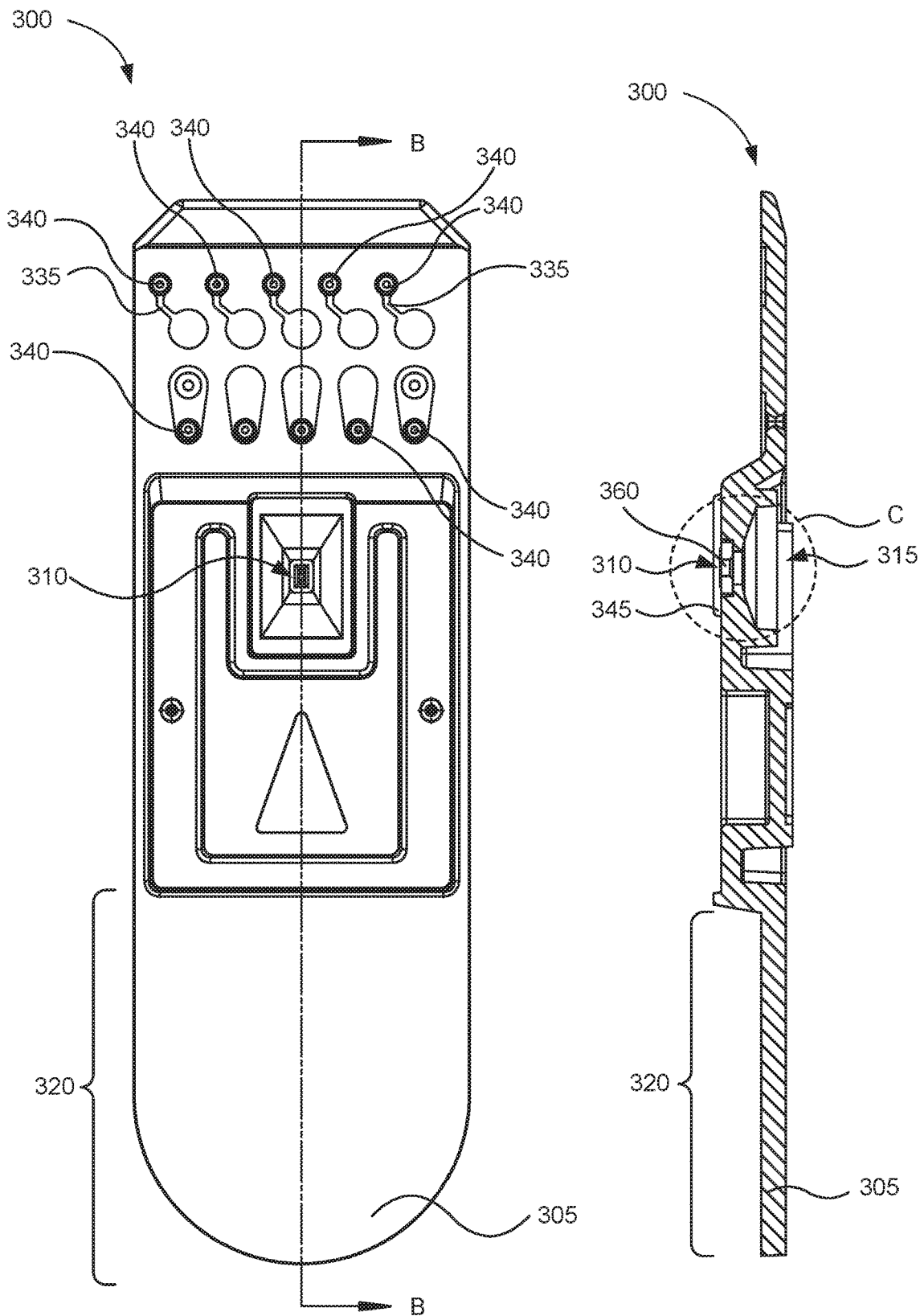
FIG. 9A is a front plan view of the cassette of FIG. 3 with a bifurcation line B according to an example of the principles described herein.
FIG. 9B is a side cutout view of the cassette of FIG. 9A with an indicating circle C according to an example of the principles described herein.

FIG. 9A is a front plan view of the cassette (300) of FIG. 3 with a bifurcation line B according to an example of the principles described herein. FIG. 9B is a side cutout view of the cassette (300) of FIG. 9A with an indicating circle C according to an example of the principles described herein. FIG. 9A includes a bifurcating line B where FIG. 9B is cut, thereby showing a cutout side view of the cassette (300). In addition to the other elements as shown in FIGS. 3-8, FIG. 9B shows a slot (360) fluidly coupling the reservoir (315) to the die (310). Additionally, FIG. 9B shows an indication circle C indicating the view presented in FIG. 9C.

Figure 9C:
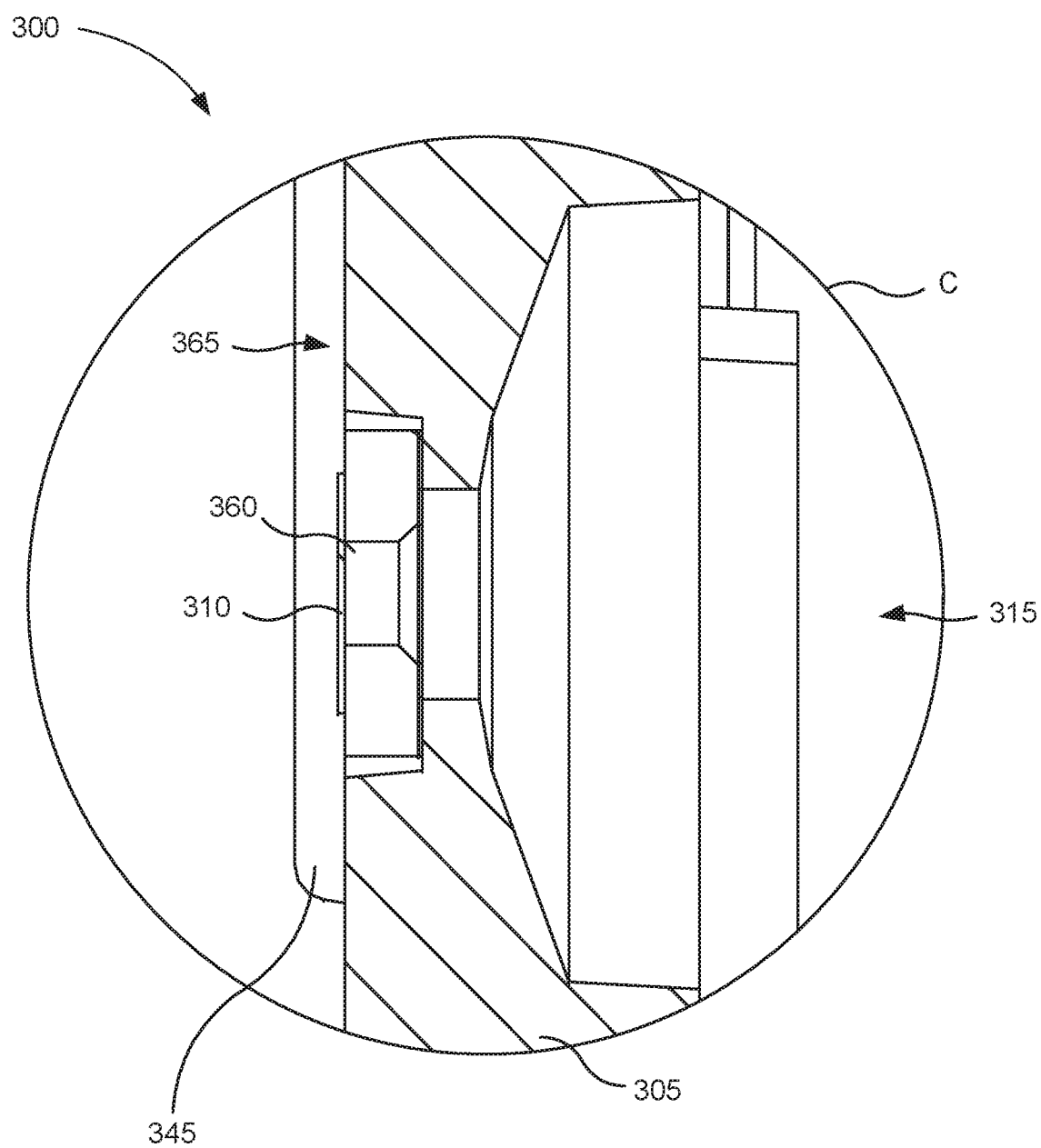
FIG. 9C is a side cutout view of the cassette of FIG. 9B according to an example of the principles described herein.

FIG. 9C is a side cutout view of the cassette (300) of FIG. 9B according to an example of the principles described herein. In addition to the other elements as shown in FIGS. 3-8, FIG. 9C shows the die (310) proud relative to a surface (365) of the substrate (305). As described above, the distance that the die (310) protrudes out from the surface (365) may be a portion of the thickness of the die (310). In an example, the distance that the die (310) protrudes out from the surface (365) may be the thickness of the die (310). In another example, the distance that the die (310) protrudes out from the surface (365) may be the thickness of the nozzle plate of the die (310) formed over the silicon as described above. In another example, the distance that the die (310)

protrudes out from the surface (365) may be 40 micrometers. In another example, the distance that the die (310) protrudes out from the surface (365) may be between 30 to 50 micrometers.

Figure 10:
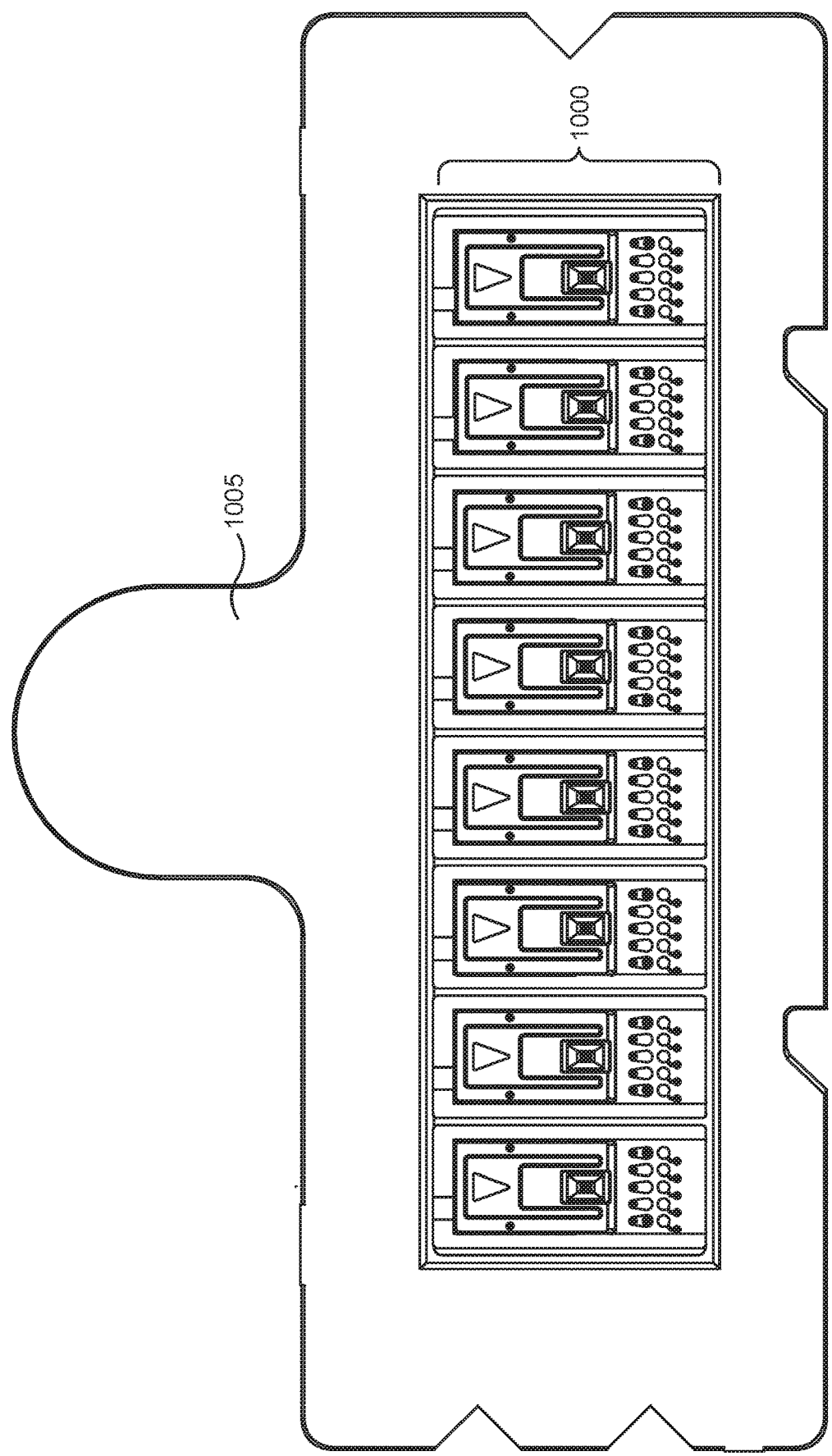
FIG. 10 is a front plan view of a number of dispense head assemblies according to an example of the principles described herein.

FIG. 10 is a front plan view of a number of dispense head assemblies (1000) according to an example of the principles described herein. Each of the dispense head assemblies (1000) may include the substrate (305), die (310), reservoir (315), handle (320), contact pads (325), contact seats (330), vias (340), traces (335), rails (345), nozzle plate (350), and nozzles (355) as described above. In the example shown in FIG. 10, the dispense head assemblies (1000) are mounted onto a frame (1005). In an example, the dispense head assemblies (1000) may be mechanically coupled to the frame (1005) by, for example, a number of clips. In an example, the frame (1005) forms the substrate (305) of each dispense head assemblies (1000) such that each of the dispense head assemblies (1000) are formed into a single monolithic frame (1005).

Figure 11:
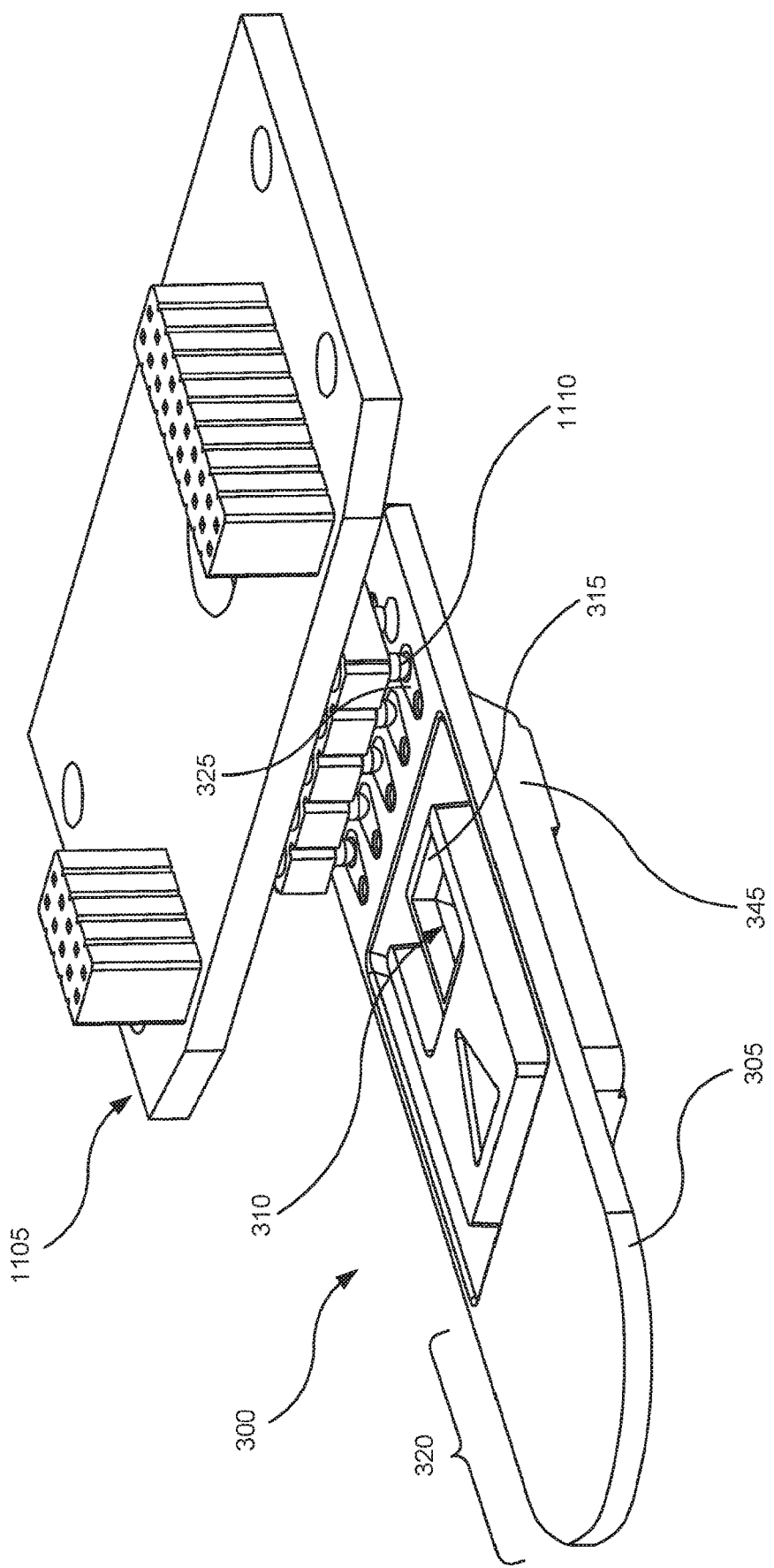
FIG. 11 is a perspective view of an interface between a cassette and a PCA according to an example of the principles described herein.

FIG. 11 is a perspective view of an interface between a cassette (300) and a PCA (1105) according to an example of the principles described herein. As described above, the PCA (1105) may include a number of pogo connectors (1110) that interface with each of the contact pads (325) defined on the cassette (300). The PCA (1105) may be a portion of the device used to control the cassette (300) and its die (310). In particular, the device that controls the cassette (300) and its die (310) may include the PCA (1105) as well as the controller as described above.

Figure 12:
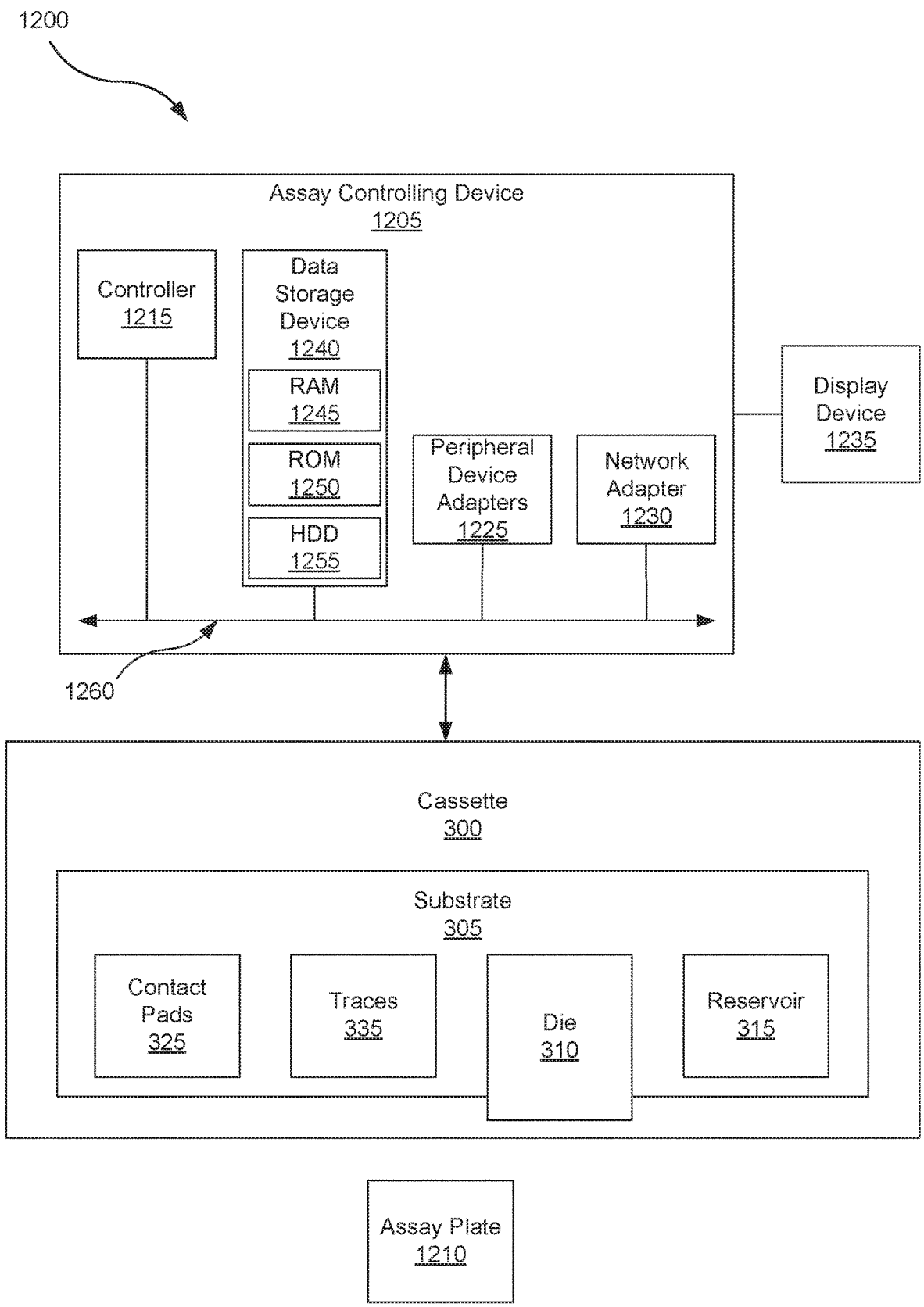
FIG. 12 is a block diagram of a system for ejecting a fluid into an assay according to an example of the principles described herein.

FIG. 12 is a block diagram of a system (1200) for ejecting a fluid into an assay according to an example of the principles described herein. The system (1200) includes an assay controlling device (1205), a cassette (300) as described above, and an assay plate (1210).

The cassette (300) may include, at least, the substrate (305), die (310), reservoir (315), contact pads (325), and traces (335) as described above. In other examples, the cassette (300) may further include the contact seats (330), vias (340), and rails (345) as also described above. Although the cassette (300) shown in FIG. 12 does or does not include certain elements as described herein, each of the elements associated with the cassette (300) may or may not be included. In order to achieve these different examples, the physical properties of the cassette (300) may be changed. For example, where the cassette (300) does not comprise the vias (340) as described above, the traces (335) and contact pads (325) may be included on a single side of the cassette (300) such that the PCA contacts the cassette (300) via the back side of the cassette (300) instead of the front.

The assay plate (1210) may be any plate that receives a fluid ejected from the die (310). The assay plate (1210) may include a number of wells into which the fluid may be ejected. The assay plate (1210) may further include a structure to which the assay controlling device (1205) may interact with the assay plate (1210) to move the assay plate (1210) relative to the die (310) of the cassette (300).

The assay controlling device (1205) may be utilized in any data processing scenario including, stand-alone hardware, mobile applications, through a computing network, or combinations thereof. Further, the assay controlling device (1205) may be used in a computing network, a public cloud network, a private cloud network, a hybrid cloud network, other forms of networks, or combinations thereof. To achieve its desired functionality, assay controlling device (1205) comprises various hardware components. Among these hardware components may be a number of controllers (1215), a number of data storage devices (1240), a number of peripheral device adapters (1225), and a number of network adapters (1230). These hardware components may be interconnected through the use of a number of busses (1260) and/or network connections. In one example, the controllers (1215), data storage devices (1240), peripheral device adapters (1225), and network adapters (1230) may be communicatively coupled via a bus (1260).

The controllers (1215) may include the hardware architecture to retrieve executable code from the data storage devices (1240) and execute the executable code. The executable code may, when executed by the controllers (1215), cause the controllers (1215) to implement at least the functionality of sending signals to the die (310) of the cassette (300) and eject an amount of fluid into an assay plate (1210) according to the methods of the present specification described herein. In the course of executing code, the controllers (1215) may receive input from and provide output to a number of the remaining hardware units.

The data storage devices (1240) may store data such as executable program code that is executed by the controllers (1215) or other processing device. As will be discussed, the data storage devices (1240) may specifically store computer code representing a number of applications that the controller (1215) executes to implement at least the functionality described herein.

The data storage devices (1240) may include various types of memory modules, including volatile and nonvolatile memory. For example, the data storage devices (1240) of the present example includes Random Access Memory (RAM) (1245), Read Only Memory (ROM) (1250), and Hard Disk Drive (HDD) memory (1255). Many other types of memory may also be utilized, and the present specification contemplates the use of many varying type(s) of memory in the data storage devices (1240) as may suit a particular application of the principles described herein. In certain examples, different types of memory in the data storage devices (1240) may be used for different data storage purposes. For example, in certain examples the controllers (1215) may boot from Read Only Memory (ROM) (1250), maintain nonvolatile storage in the Hard Disk Drive (HDD) memory (108), and execute program code stored in Random Access Memory (RAM) (1245).

Generally, the data storage devices (1240) may comprise a computer readable medium, a computer readable storage medium, or a non-transitory computer readable medium, among others. For example, the data storage devices (1240) may be, but not limited to, an electronic, magnetic, optical, electromagnetic, infrared, or semiconductor system, apparatus, or device, or any suitable combination of the foregoing. More specific examples of the computer readable storage medium may include, for example, the following: an electrical connection having a number of wires, a portable computer diskette, a hard disk, a random-access memory (RAM), a read-only memory (ROM), an erasable programmable read-only memory (EPROM or Flash memory), a portable compact disc read-only memory (CD-ROM), an optical storage device, a magnetic storage device, or any suitable combination of the foregoing. In the context of this document, a computer readable storage medium may be any tangible medium that may contain, or store computer usable program code for use by or in connection with an instruction execution system, apparatus, or device. In another example, a computer readable storage medium may be any non-transitory medium that may contain, or store a program for use by or in connection with an instruction execution system, apparatus, or device.

The hardware adapters (1225, 1230) in the assay controlling device (1205) enable the controllers (1215) to interface with various other hardware elements, external and internal to the assay controlling device (1205). For example, the peripheral device adapters (1225) may provide an interface to input/output devices, such as, for example, a display device, a mouse, or a keyboard. The peripheral device adapters (1225) may also provide access to other external devices such as an external storage device, a number of network devices such as, for example, servers, switches, and routers, client devices, other types of computing devices, and combinations thereof.

The display device (1235) may be provided to allow a user of the assay controlling device (1205) to interact with and implement the functionality of the assay controlling device (1205). The peripheral device adapters (1225) may also create an interface between the controllers (1215) and the display device (1235), a printer, or other media output devices. The network adapter (1230) may provide an interface to other computing devices within, for example, a network, thereby enabling the transmission of data between the assay controlling device (1205) and other devices located within the network.

The assay controlling device (1205) may, when executed by the controllers (1215), display the number of graphical user interfaces (GUIs) on the display device (1235) associated with the executable program code representing the number of applications stored on the data storage devices (1240). Examples of display devices (1235) include a computer screen, a laptop screen, a mobile device screen, a personal digital assistant (PDA) screen, and a tablet screen, among other display devices (1235). Examples of the GUIs displayed on the display device (1235), will be described in more detail below.

The assay controlling device (1205) further comprises a number of modules used in the implementation of the methods described herein. The various modules within the assay controlling device (1205) comprise executable program code that may be executed separately. In this example, the various modules may be stored as separate computer program products. In another example, the various modules within the assay controlling device (1205) may be combined within a number of computer program products; each computer program product comprising a number of the modules.

FIG. 13 is a flowchart depicting a method (1300) of forming a cassette (300) according to an example of the principles described herein. The method (1300) may begin with forming (1305) a monolithic substrate wherein the substrate includes a reservoir (FIG. 1, 115) defined in a first surface of the substrate (FIG. 1, 105) and a slot (FIG. 9B, 360) defined in a second surface of the substrate (105) with the reservoir (FIG. 1, 115) and the slot (FIG. 9B, 360) being fluidically coupled. The method (1300) may further include coupling (1310) a fluid ejection die (FIG. 3, 310) to the slot (FIG. 9B, 360) wherein at least a portion of the fluid ejection die (FIG. 3, 310) is proud relative to at least one surface of the substrate (FIG. 1, 105).

In an example, the method (1300) may further include forming at least one rail (345) on the at least one surface of the substrate, wherein the at least one rail (345) protrudes past a plane of a distal surface of the die (110), and wherein a thickness of the at least one rail (345) relative to the at least one surface of the substrate (105) defines a minimal distance between the distal surface of the die (110) and an assay into which the die (110) ejects a fluid.

Aspects of the present system and method are described herein with reference to flowchart illustrations and/or block diagrams of methods, apparatus (systems) and computer program products according to examples of the principles described herein. Each block of the flowchart illustrations and block diagrams, and combinations of blocks in the flowchart illustrations and block diagrams, may be implemented by computer usable program code. The computer usable program code may be provided to a processor of a general-purpose computer, special purpose computer, or other programmable data processing apparatus to produce a machine, such that the computer usable program code, when executed via, for example, the controller (1215) of the assay controlling device (1205) or other programmable data processing apparatus, implement the functions or acts specified in the flowchart and/or block diagram block or blocks. In one example, the computer usable program code may be embodied within a computer readable storage medium; the computer readable storage medium being part of the computer program product. In one example, the computer readable storage medium is a non-transitory computer readable medium.

The specification and figures describe a cassette that includes a proud die relative to a surface of the cassette. The cassette, system, and methods described herein provide for a cassette that places the die closer to an assay plate. This may prevent errant sprays of fluid into parts of the assay plate that the fluid should not be ejected to. Consequently, a more precise chemical analysis or assay analysis may be completed without the concern that the results may not be as accurate. A number of rails may also be placed on the surface of the cassette such that objects may not touch the die.

The preceding description has been presented to illustrate and describe examples of the principles described. This description is not intended to be exhaustive or to limit these principles to any precise form disclosed. Many modifications and variations are possible in light of the above teaching.

What is claimed is:

1. A cassette comprising:
a substrate;
a die coupled to the substrate; and
a reservoir defined in the substrate exposing a proximal side of the die to an external atmosphere,
wherein at least a portion of the die is proud relative to at least one surface of the substrate.

2. The cassette of claim 1, wherein the distance from a distal surface of the die relative to the at least one surface of the substrate is approximately 40 micrometers.

3. The cassette of claim 1, wherein the distance from a distal surface of the die relative to the at least one surface of the substrate is between a portion of a thickness of the die and the thickness of the die.

4. The cassette of claim 1, further comprising at least one rail formed on the at least one surface of the substrate, wherein the at least one rail protrudes past a plane of a distal surface of the die.

5. The cassette of claim 4, wherein a thickness of the at least one rail relative to the at least one surface of the substrate defines a minimal distance between the distal surface of the die and an assay into which the die ejects a fluid.

6. The cassette of claim 1, wherein the reservoir is formed on an opposite side of the substrate from the die, and the cassette further comprises at least one slot fluidically coupling the reservoir to the die through the substrate.

7. A system for ejecting a fluid into an assay comprising:
at least one dispense head, the at least one dispense head comprising:

a substrate;

a die coupled to the substrate; and a reservoir defined in the substrate exposing a proximal side of the die to an external atmosphere; and a controller to instruct the die to eject an amount of the fluid;

wherein a distance from a distal surface of the die relative to a surface of the substrate from which the die protrudes is approximately 40 micrometers.

8. The system of claim 7, wherein a plurality of dispense heads are included within the system, the dispense heads being integrated into a frame.

9. The system of claim 7, further comprising at least one rail formed on the at least one surface of the substrate, wherein the at least one rail protrudes past a plane of the distal surface of the die.

10. The system of claim 9 wherein a thickness of the at least one rail relative to the at least one surface of the substrate defines a minimal distance between the distal surface of the die and an assay into which the die ejects a fluid.

11. The system of claim 7, further comprising at least one slot fluidically coupling the reservoir to the die through the substrate.

12. A cassette comprising:

a substrate;

a die coupled to the substrate; and a reservoir defined in the substrate exposing a proximal side of the die to an external atmosphere, wherein at least a portion of the die is proud relative to at least one surface of the substrate between approximately 30 and 50 micrometers.

13. The cassette of claim 12, wherein the distance from a distal surface of the die relative to the at least one surface of the substrate is approximately 40 micrometers.

14. The cassette of claim 12, wherein the distance from a distal surface of the die relative to the at least one surface of the substrate is between a portion of a thickness of the die and the thickness of the die.

15. The cassette of claim 12, further comprising:

at least one rail on the at least one surface of the substrate, wherein the at least one rail protrudes past a plane of a distal surface of the die, and wherein a thickness of the at least one rail relative to the at least one surface of the substrate defines a minimal distance between the distal surface of the die and an assay into which the die ejects a fluid.

* * * * *